United States Patent
Cella et al.

(10) Patent No.: US 7,241,851 B2
(45) Date of Patent: Jul. 10, 2007

(54) SILICONE CONDENSATION REACTION

(75) Inventors: James Anthony Cella, Clifton Park, NY (US); Slawomir Rubinsztajn, Niskayuna, NY (US)

(73) Assignee: Momentive Performance Materials Inc., Wilton, CT (US)

( * ) Notice: Subject to any disclaimer, the term of this patent is extended or adjusted under 35 U.S.C. 154(b) by 258 days.

(21) Appl. No.: 10/918,608

(22) Filed: Aug. 12, 2004

(65) Prior Publication Data

US 2005/0033001 A1 Feb. 10, 2005

(51) Int. Cl.
C08G 77/08 (2006.01)
(52) U.S. Cl. ............................ 528/13; 528/29; 528/25; 528/26; 528/19; 528/21; 556/470; 556/466; 556/401
(58) Field of Classification Search ................ 556/470, 556/466, 401; 528/13, 29, 25, 26, 19, 21
See application file for complete search history.

(56) References Cited

U.S. PATENT DOCUMENTS

| | | | | |
|---|---|---|---|---|
| 2,731,485 A | * | 1/1956 | Wagner et al. | 556/460 |
| 2,967,171 A | * | 1/1961 | Barnes, Jr. et al. | 528/15 |
| 3,069,451 A | * | 12/1962 | Fritz | 556/470 |
| 3,846,463 A | * | 11/1974 | Nagai et al. | 556/443 |
| 3,856,843 A | * | 12/1974 | Nagai et al. | 556/463 |
| 4,026,827 A | * | 5/1977 | Steffen | 528/14 |
| 4,332,654 A | * | 6/1982 | Yates | 204/157.74 |
| 5,767,216 A | * | 6/1998 | Frances et al. | 528/17 |
| 2003/0139287 A1 | | 7/2003 | Deforth et al. | |
| 2003/0195370 A1 | | 10/2003 | Taylor et al. | |

FOREIGN PATENT DOCUMENTS

EP 0 291 871 A 11/1988

OTHER PUBLICATIONS

Parks et al. Studies on the Mechanism of B(C6F5)3 Catalyzed Hydrosilation of Carbonyl Functions, J. Org. Chem. 2000, 65, 3090-3098.*

* cited by examiner

*Primary Examiner*—Margaret G. Moore
(74) *Attorney, Agent, or Firm*—Dominick G. Vicari

(57) ABSTRACT

A new silicone condensation reaction, the condensation between an alkoxy silane or siloxane or a dihydric phenol and an organo-hydrosilane or siloxane and catalysts therefore is described and claimed.

8 Claims, No Drawings

SILICONE CONDENSATION REACTION

The present invention relates to a new condensation reaction between compounds containing the hydrogen bonded directly to silicon (organo-hydrosilanes or organo-hydrosiloxanes) and alkoxy-silane or siloxane which leads to the formation of siloxane bond and release of hydrocarbons as a by-product or dihydric phenols which leads to the formation of polyaryloxysilanes or polyaryloxysiloxanes

BACKGROUND OF THE INVENTION

Two general processes can be applied for synthesis of organosiloxane polymers; ring opening polymerization of cyclic siloxanes and polycondensation. The polycondensation reaction between organofunctional silanes or oligosiloxanes leads to the formation of siloxane bond and elimination of a low molecular byproduct. The polycondensation of low molecular weight siloxanol oils is the most common method synthesis of polyorganosiloxanes and has been practiced for several years. The byproduct of this process is water. Unfortunately this method cannot be used for the synthesis of well-defined block organosiloxane copolymers. In that case the non-hydrolytic condensation processes can be employed. Many of such reactions are known and are frequently used:
1) the reaction of an organohalosilane with an organoalkoxysilane, ≡Si—X+R—O—Si≡→≡Si—O—Si≡+RX;
2) the reaction of organohalosilanes with organoacyloxysilanes, ≡Si—X+RCOO—Si≡→≡Si—O—Si≡+RCOX;
3) the reaction of organohalosilanes with organosilanols, ≡Si—X+HO—Si≡→≡Si—O—Si≡+HX;
4) the reaction of organohalosilanes with metal silanolates, ≡Si—X+Metal—O—Si≡→≡Si—O—Si≡+MetalX;
5) the reaction of organo-hydrosilanes with organosilanols, ≡Si—H+HO—Si≡→≡Si—O—Si≡+$H_2$;
6) the self-reaction of organoalkoxysilanes, ≡Si—OR+RO—Si≡→≡Si—O—Si≡+ROR
7) the reaction of organoalkoxysilanes with organoacyloxysilanes, ≡Si—OR+R'COO—Si≡→≡Si—O—Si≡+R'COOR
8) the reaction of organoalkoxysilanes with organosilanols, ≡Si—OR+HO—Si≡→≡Si—O—Si≡+ROH
9) the reaction of organoaminosilanes with organosilanols, ≡Si—$NR_2$+HO—Si≡→≡Si—O—Si≡+$NR_2H$;
10) the reaction of organoacyloxysilanes with metal silanolates, ≡Si—OOR+Metal—O—Si≡→≡Si—O—Si≡+MetalOOR;
11) the reaction of organoacyloxysilanes with organosilanols, ≡Si—OOR+HO—Si≡→≡Si—O—Si≡+HOOR;
12) the reaction of organooximesilane with organosilanols, ≡Si—ON=$OR_2$+HO—Si≡→≡Si—O—Si≡+HN=$OR_2$;
13) the reaction of organoenoxysilane with organosilanols, ≡Si—O(C=$CH_2$)R+HO—Si≡→≡Si—O—Si≡+$CH_3COR$;

Those reactions can also be used for the formation of siloxane networks via a crosslinking process. Many of the above processes require the presence of catalyst such as protic acids, Lewis acids, organic and inorganic bases, metal salts and organometalic complexes. (See, for example, (a) "The Siloxane Bond" Ed. Voronkov, M. G. ; Mileshkevich, V. P. ; Yuzhelevskii, Yu. A. Consultant Bureau, New York and London, 1978; and (b) Noll, W. "Chemistry and Technology of Silicones", Academia Press, New York, 1968).

It is also well known in silicon chemistry that the organosilanol moiety will react with a hydrogen atom bonded directly to silicon (organo-hydrosilane) to produce a hydrogen molecule and the silicon-oxygen bond, (See, "Silicon in Organic, Organometallic and Polymer Chemistry" Michael A. Brook, John Wiley & Sons, Inc. , New York, Chichester, Weinheim, Brisbane, Singapore, Toronto, 2000). Although the uncatalyzed reaction will run at elevated temperatures, it is widely known that this reaction will run more readily in the presence of a transition metal catalyst especially noble metal catalysts such as those comprising platinum, palladium, etc. , a basic catalyst such as an alkali metal hydroxide, amine, etc. , or a Lewis acid catalyst such as a tin compound, etc. Recently it has been reported that organoboron compounds are extremely efficient catalysts for the reaction between an organo-hydrosilanes and organosilanols (WO 01/74938 A1). Unfortunately, the by-product of this process is dangerous, highly reactive hydrogen.

Another useful class of materials, polyaryloxysilanes (PAS) have long been materials of commercial interest. In addition to the property benefits expected for any silicone copolymer, such as good low temperature flexibility, high temperature stability PAS also exhibit excellent flammability characteristics.

These polymers are commonly prepared by the reaction of bis-phenols with α, ω-difunctional silanes, typically, α, ω-dichlorosilanes or α, ω-diaminosilanes. Reaction of bis-phenols with α, ω-dichlorosilanes requires the use of a stoichiometric amount of an acid acceptor, usually a tertiary amine. As the ether linkage in these polymers is susceptible to hydrolysis, particularly in the presence of acid or base, the amine and its salts must be completely removed from the polymer for optimal stability. The α, ω-diaminosilanes do not require an acid scavenger during the preparation of the polymer, but these intermediates themselves are prepared by the reaction of chlorosilanes with amines in the presence of an acid acceptor.

In spite of the foregoing developments, there is a continuing search for new condensation reactions that will improve reaction's selectivity and safety of the polycondensation process.

SUMMARY OF THE INVENTION

The present invention provides a new condensation process for forming a silicon-oxygen bond comprising reacting an organosilane or siloxane compounds bearing at least one hydrosilane functional group with an organoalkoxysilane or siloxane compounds containing at least one alkoxysilane functional group and release of hydrocarbon as a byproduct, in the presence of a Lewis acid catalyst. The present invention also provides for the formation of silicon-oxygen bond by reacting a compound comprising both at least one hydrosilane functionality and at least one an alkoxysilane moiety and releases hydrocarbon as a byproduct in the presence of a Lewis acid catalyst.

Thus the present invention provides for a process for forming a silicon to oxygen bond comprising: (a) reacting a first silicon containing compound said first silicon containing compound comprising a hydrogen atom directly bonded to a silicon atom with (b) a second silicon containing compound said second silicon containing compound comprising an alkoxy group bonded to a silicon atom, in the presence of (c) a Lewis acid catalyst thereby forming a silicon to oxygen bond. The present invention also provides for a process for forming an silicon to oxygen bond comprising: (a) selecting a compound comprising both at least one hydrogen atom directly bonded to a silicon atom and at least one an alkoxy group bonded to a silicon atom in said compound and (b) reacting the hydrosilane functional group with the alkoxysilane group, in the presence of (c) a Lewis acid catalyst thereby forming a silicon to oxygen bond. The present invention also provides for a process for forming a silicon to oxygen bond comprising: (a) selecting a compound comprising at least one hydrosilane functional group and a second compound serving as a source of oxygen such as water, alcohol, aldehydes, ethers, and esters (b) reacting the hydrosilane functional group with the a second compound, in the presence of (c) a Lewis acid catalyst thereby forming a silicon to oxygen to carbon bond which subsequently reacts with the residual hydrosilane functional group to form new silicon to oxygen bond.

The present invention also provides for a process for forming a silicon to oxygen bond that is part of a polyaryloxysilane or polyaryloxysiloxane comprising: (a) selecting a compound comprising at least two hydrosilane functional groups and a second compound comprising at least one of a diphenolic compound or dialkylether of a diphenolic compound (b) reacting the hydrosilane functional group with the a second compound, in the presence of (c) a Lewis acid catalyst thereby forming a silicon to oxygen to carbon bond.

The processes of the present invention further provide for means to produce compositions: siloxane foams, hyperbranched silicone polymers, cross-linked siloxane networks and gels therefrom as well as other silicone and siloxane molecules exemplified herein.

DETAILED DESCRIPTION OF THE INVENTION

The present invention represents the discovery of a new type of non-hydrolytic condensation reaction for silicon bearing molecules. Generally, the reaction may be characterized as a condensation reaction between an organo hydrosilane or siloxane compounds bearing at least one hydrosilane moiety with an organoalkoxysilane or siloxane compounds containing at least one alkoxysilane moiety or functionality in the following exemplary embodiment: the reaction of $(M_aD_bT_cQ_d)_e(R^2)_f(R^3)_g SiOCH_2R^1$ and $HSi(R^4)_h(R^5)_i(M_aD_bT_cQ_d)_j$ yields a compound containing a new silicon-oxygen bond $(M_aD_bT_cQ_d)_e(R^2)_f(R^3)_g SiOSi(R^4)_h(R^5)_i(M_aD_bT_cQ_d)_j$ and hydrocarbon $(CH_3R^1)$ as the products. The subscripts a, b, c and d are independently zero or positive number; e, f, g, h, i, j are zero or positive number subject to limitation that e+f+g=3; h+i+j=3; j=0, 1, 2; i=0, 1, or 2 subject to the limitation that i+j≦2. The other molecular components have standard definitions as follows:

$M = R^6R^7R^8SiO_{1/2}$;

$D = R^9R^{10}SiO_{2/2}$;

$T = R^{11}SiO_{3/2}$; and $Q = SiO_{4/2}$ or drawn as structures (without any implied limitations of stereochemistry):

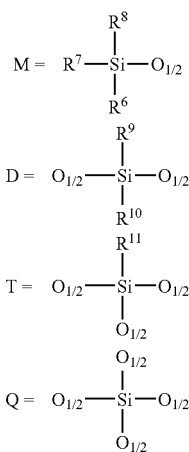

The $R^1$ substituent is hydrogen or is independently selected from the group of one to sixty carbon atom monovalent hydrocarbon radicals that may or may not be substituted with halogens (halogen being F, Cl, Br and I), e.g. non limiting examples being fluoroalkyl substituted or chloroalkyl substituted, substituents $R^2$, $R^4$, $R^6$, $R^7$, $R^8$, $R^9$, $R^{10}$, and $R^{11}$ are independently selected from the group of one to sixty carbon atom monovalent hydrocarbon radicals that may or may not be substituted with halogens (halogen being F, Cl, Br and I), e.g. non limiting examples being fluoroalkyl substituted or chloroalkyl substituted and $R^3$ and $R^5$ are independently selected from the group consisting of hydrogen, one to sixty carbon atom monovalent alkoxy radicals, one to sixty carbon atom monovalent aryloxy radicals, one to sixty carbon atom monovalent alkaryloxy radicals and halogen.

Condensation of molecules that bear both functionalities, one ($\equiv SiOCH_2R^1$) and one (H—Si$\equiv$), on the same molecular backbone will lead to a formation of linear polymers unless the condensation reaction is conducted with a highly diluted substrate, in which case cyclic condensation products would be expected. Molecules that bear more than one ($\equiv SiOCH_2R^1$) and only one (H—Si$\equiv$) functionalities on the same molecular backbone as well as molecules that bear one ($\equiv SiOCH_2R^1$) and more than one (H—Si$\equiv$) functionalities on the same molecular backbone are examples of $AB_x$ molecular structures. The condensation of these $AB_x$ compounds will lead to a formation of complex hyperbranched condensation polymers. The examples of such $AB_x$ molecular structures include but are not limited to:

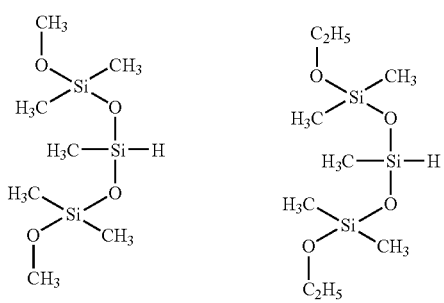

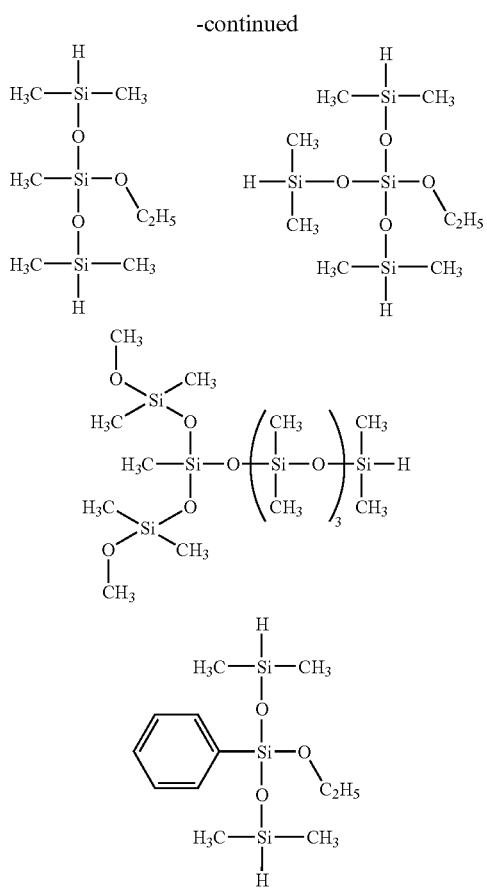

Condensation of siloxane oligomers and polymers that bear more than one (≡SiOCH$_2$R$^1$) functional group with the siloxane oligomers and polymers having more than one (H—Si≡) functionality is also possible and will lead to a formation of the cross-linked network. A preferred structure of the polymers with (≡SiOCH$_2$R$^1$) groups has the following formula:

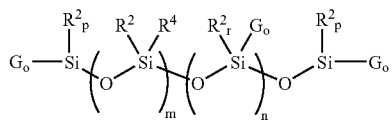

where G is OCH$_2$R$^1$; R$^1$, R$^2$, R$^4$ has been defined before, m=0, 1, 2 . . . 5000; n=0, 1, 2 . . . 1000; o=1, 2, 3; p=0, 1, 2, 3; r=0, 1, 2 with limitation that r+o=2 for internal siloxane and p+o=3 for terminal siloxane units.

A preferred structure of the polymer with (≡Si—H) groups has the following formula:

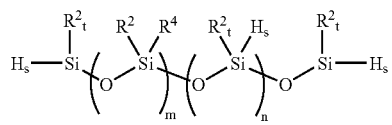

where R$^1$, R$^2$, R$^4$ has been defined before, m=0, 1, 2 . . . 1000; n=0, 1, 2 . . . 100; t =0, 1, 2, 3 s=0, 1, 2, 3 with the limitation that t+s=2 for internal siloxane units and t+s=3 for terminal siloxane units.

Other preferred compounds with (≡Si—H) groups are: Cyclic siloxanes:

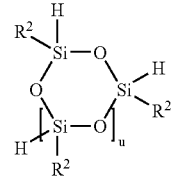

where R$^2$ has been defined before and u=1, 2, 3 . . . 8; or branched siloxane:

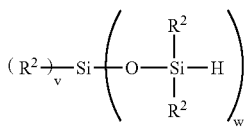

where R$^2$ has been defined before and v=0, 1; w=3, 4

Condensation of siloxane oligomers and polymers that bear more than one (≡SiOCH$_2$R$^1$) moiety and more than one (H—Si≡) functionality is also possible and will lead to formation of a cross-linked network.

Condensation of diphenolic compounds and compounds with compounds having two H—Si≡ functionalities will lead to the formation of polysilylarylethers:

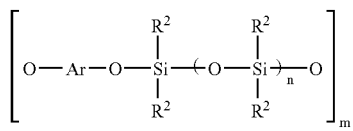

where Ar represents a typical bis-phenol species as described herein, R$^2$ has been defined previously, n=0–400 and m= about 10–200

The above reactions are generally accomplished in the presence of an appropriate catalyst. The catalyst for this reaction is preferably a Lewis acid catalyst. For the purposes herein, a "Lewis acid" is any substance that will take up an electron pair to form a covalent bond (i.e., "electron-pair acceptor"). This concept of acidity also includes the "proton donor" concept of the Lowry-Bronsted definition of acids. Thus boron trifluoride (BF$_3$) is a typical Lewis acid, as it contains only six electrons in its outermost electron orbital shell. BF$_3$ tends to accept a free electron pair to complete its eight-electron orbital. Preferred Lewis acid catalysts include such catalysts as FeCl$_3$, AlCl$_3$, ZnCl$_2$, ZnBr$_2$, BF$_3$. The ability of any particular Lewis acid to catalyze the new reaction of the present invention will be a function of acid strength, steric hindrance of both the acid and the substrate and solubility of the Lewis acid and the substrate in the reaction medium. Generally the following Lewis acids: FeCl$_3$, AlCl$_3$, ZnCl$_2$, ZnBr$_2$, and BF$_3$ are only sparingly soluble in siloxane solvents and this low solubility tends to interfere with the ability of these particular Lewis acid catalysts to catalyze the desired reaction. Lewis acid catalysts having a greater solubility in siloxane media are more preferred and preferable catalysts include Lewis acid catalysts of formula (I)

$$MR^{12}_xX_y \qquad (I)$$

wherein M is B, Al, Ga, In or Tl; each $R^{12}$ is independently the same (identical) or different and represent a monovalent aromatic hydrocarbon radical having from 6 to 14 carbon atoms, such monovalent aromatic hydrocarbon radicals preferably having at least one electron-withdrawing element or group such as —$CF_3$, —$NO_2$ or —CN, or substituted with at least two halogen atoms; X is a halogen atom; x is 1, 2, or 3; and y is 0, 1 or 2; with the proviso that x+y=3, more preferably a Lewis acid of Formula (II)

$$BR^{13}_xX_y \qquad (II)$$

wherein each $R^{13}$ are independently the same (identical) or different and represent a monovalent aromatic hydrocarbon radical having from 6 to 14 carbon atoms, such monovalent aromatic hydrocarbon radicals preferably having at least one electron-withdrawing element or group such as —$CF_3$, —$NO_2$ or —CN, or substituted with at least two halogen atoms; X is a halogen atom; x is 1, 2, or 3; and y is 0, 1 or 2; with the proviso that x+y=3, and is most preferably $B(C_6F_5)_3$.

The condensation reaction between the (≡Si—H) moiety and the (≡SiOR) moiety has some limitations, it appears that when three electron withdrawing substituents are on the silicon containing (≡Si—H) bond such as for example—OR, siloxane substituents or X (X=halogen) the reaction kinetics are slowed, sometimes to the point of inhibition of the reaction. Also the condensation reaction appears to require an alkoxy silane of the following structure (≡Si—O—$CH_2$—$R^1$) wherein $R^1$ is $C_{1-60}$ alkyl, $C_{1-60}$ alkoxy, $C_{2-60}$ alkenyl, $C_{6-60}$ aryl, and $C_{6-60}$ alkyl-substituted aryl, and $C_{6-60}$ arylalkyl where the alkyl groups may be halogenated, for example, fluorinated to contain fluorocarbons such as $C_{1-22}$ fluoroalkyl. The preferred alkoxy group is methoxy and ethoxy group.

The process of the present invention utilizes a Lewis acid catalyst concentration that ranges from about 1 part per million by weight to about 10 weight percent (based on the total weight of siloxanes being reacted); preferably from about 10 part per million by weight (wppm) to about 5 weight percent (50,000 wppm), more preferably from about 50 wppm to about 10,000 wppm and most preferably from about 50 wppm to about 5,000 wppm.

The condensation reaction can be done without solvent or in the presence of solvents. The presence of solvents may be beneficial due to an increased ability to control viscosity, rate of the reaction and exothermicity of the process. The preferred solvents include aliphatic hydrocarbons, aromatic hydrocarbons, halogenated hydrocarbons, as well as oligomeric cyclic diorganosiloxanes.

The condensation reaction between the (≡Si—H) moiety and the (≡SiOCH$_2$R$^1$) moiety can be conducted at an ambient or at an elevated temperature depending on the chemical structures of reagents and catalysts, concentration of catalyst and used solvent.

In some cases it is desirable to blend siloxane oligomers or polymers that bear at least one (≡SiOCH$_2$R$^1$) moiety with the siloxane oligomers or polymers having at least one (H—Si≡) functional group and Lewis acid catalyst. Subsequently the condensation reaction may be activated by heat. To extend the pot life of such a fully formulated mixture, the addition of a stabilizing agent is recommended. The stabilizing additives that are effective belong to the group of nucleophiles that are able to form a complex with Lewis acids. These stabilizing additives, preferably nucleophilic compounds, include but are not limited to ammonia, primary amines, secondary amines, tertiary amines, organophosphines and phosphines.

In yet another embodiment, a polyaryloxysilane or polyaryloxysiloxane is produced from a reaction of stoichiometric amounts of an organohydrosilane or siloxane compound bearing at least two hydrosilane moieties, such as but not limited to 1,1,3,3-tetramethyldisiloxane or diphenylsilane, with a diphenolic compound or an dialkylether of a diphenolic compound. Compounds being such diphenolic or diphenolic ethers include but are not limited to: bis-phenol A, hydroquinone and dialkylethers of hydroquinone, resorcinol, biphenol and dialkylethers of biphenol and compounds of the like. Preferably, the dipenolic compound is 4,4'biphenol and substituted 4,4'biphenol. Additionally, the diphenolic compound, or species, may include, but is not limited to the following:

4-bromoresorcinol
4,4'-dihydroxybiphenyl ether
4,4-thiodiphenol
1,6-dihydroxynaphthalene
2,6-dihydroxynaphthalene
bis(4-hydroxyphenyl)methane
bis(4-hydroxyphenyl)diphenylmethane
bis(4-hydroxyphenyl)-1-naphthylmethane
1,1-bis(4-hydroxyphenyl)ethane
1,1-bis(4-hydroxyphenyl)propane
1,2-bis(4-hydroxyphenyl)ethane
1,1-bis(4-hydroxyphenyl)-1-phenylethane
1,1-bis(3-methyl-4-hydroxyphenyl)-1-phenylethane
2-(4-hydroxyphenyl)-2-)3-hydroxyphenyl)propane
2,2-bis(4-hydroxyphenyl)butane
1,1-bis(4-hydroxyphenyl)isobutane
1,1-bis(4-hydroxyphenyl)decane
1,1-bis(3,5-dimethyl-4-hydroxyphenyl)cyclohexane
1,1-bis(3,5-dibromo-4-hydroxyphenyl)cyclohexane
1,1-bis(4-hydroxyphenyl)cyclohexane
1,1-bis(4-hydroxyphenyl)cyclododecane
1,1-bis(3,5-dimethyl-4-hydroxyphenyl)cyclododecane
trans-2,3-bis(4-hydroxyphenyl)-2-butene
4,4-dihydroxy-3,3-dichlorodiphenyl ether
4,4-dihydroxy-2,5-dihydroxy diphenyl ether
2,2-bis(4-hydroxyphenyl)adamantane
α, α'-bis(4-hydroxyphenyl)toluene
bis(4-hydroxyphenyl)acetonitrile
2,2-bis(3-methyl-4-hydroxyphenyl)propane
2,2-bis(3-ethyl-4-hydroxyphenyl)propane
2,2-bis(3-n-propyl-4-hydroxyphenyl)propane
2,2-bis(3-isopropyl-4-hydroxyphenyl)propane
2,2-bis(3-sec-butyl-4-hydroxyphenyl)propane
2,2-bis(3-t-butyl-4-hydroxyphenyl)propane
2,2-bis(3-cyclohexyl-4-hydroxyphenyl)propane
2,2-bis(3-allyl-4-hydroxyphenyl)propane
2,2-bis(3-methoxy-4-hydroxyphenyl)propane
2,2-bis(3,5-dimethyl-4-hydroxyphenyl)propane
2,2-bis(2,3,5,6-tetramethyl-4-hydroxyphenyl)propane
2,2-bis(3-5-dichloro-4-hydroxyphenyl)propane
2,2-bis(3,5-dibromo-4-hydroxyphenyl)propane
2,2-bis(2,6-dibromo-3,5-dimethyl-4-hydroxyphenyl)propane
α, α-bis(4-hydroxyphenyl)toluene
α, α, α', α'-Tetramethyl-α, α'-bis(4-hydroxyphenyl)-p-xylene 1,1-dichloro-2,2-bis(4-hydroxyphenyl)ethylene
1,1-dibromo-2,2-bis(4-hydroxyphenyl)ethylene
1,1-dichloro-2,2-bis(5-phenoxy-4-hydroxyphenyl)ethylene
4,4'-dihydroxybenzophenone
3,3-bis(4-hydroxyphenyl)-2-butanone
1,6-bis(4-hydroxyphenyl)-1,6-hexanedione
ethylene glycol bis(4-hydroxyphenyl)ether
bis(4-hydroxyphenyl)ether
bis(4-hydroxyphenyl)sulfide
bis(4-hydroxyphenyl)sulfoxide
bis(4-hydroxyphenyl)sulfone
bis(3,5-dimethyl-4-hydroxyphenyl)sulfone
9,9-bis(4-hydroxyphenyl)fluorene
2,7-dihydroxypyrene
6,6'-dihydroxy-3,3,3',3'-tetramethylspiro(bis)indane("spiro-biindane Bisphenol")
3,3-bis(4-hydroxyphenyl)phthalide
2,6-dihydroxydibenzo-p-dioxin
2,6-dihydroxythianthrene
2,7-dihydroxyphenoxathiin
2,7-dihydroxy-9,10-dimethylphenazine
3,6-dihydroxydibenzofuran
3,6-dihydroxydibenzothiophene
2,7-dihydroxycarbazole.

The dihydric phenols may be used alone or as mixtures of two or more dihydric phenols. Further illustrative examples of dihydric phenols include the dihydroxy-substituted aromatic hydrocarbons disclosed in U.S. Pat. No. 4,217,438.

This reaction is generally accomplished in the presence of a Lewis acid catalyst, such as those described herein. Preferably the Lewis acid catalyst is $B(C_6F_5)_3$. This process may occur at room temperature or at elevated temperatures. The catalyst concentration is the same as described previously.

In yet another embodiment, the organoalkoxysilane or siloxane compound containing at least one alkoxysilane moiety or functionality is produced from a reaction of the organohydrosilane or siloxane compounds bearing at least one hydrosilane moiety with a source of oxygen. The source of oxygen may be any compound that reacts with the organohydrosilane or siloxane compounds bearing at least one hydrosilane moiety to produce an organoalkoxysilane or siloxane compound containing at least one alkoxysilane moiety or functionality.

The organohydrosilane or siloxane compounds bearing at least one hydrosilane moiety or functionality are generally those silanes and siloxanes of the strictures provided above. The oxygen source preferably includes any molecule that could be reduced in the presence of a ($\equiv$Si—H) moiety and a catalyst. Compounds being such oxygen sources include but are not limited to alcohols, ethers, aldehydes, carbonates and esters. Preferably, the oxygen source is any alkyl ether, alkyl alcohol alkyl or aryl aldehyde, alkyl ester, more preferably the oxygen source is a dialkyl ether, such as diethyl ether, alkyl ester such as methyl acetate, ethyl acetate, alkyl carbonate such as dimethyl carbonate.

The above reaction is generally accomplished in the presence of an appropriate catalyst. The catalyst for this reaction is preferably the same type of catalyst as described previously, namely the Lewis acid catalysts described herein and more preferably, $B(C_6F_5)_3$. The above reaction can be accomplished in ambient conditions or at elevated temperature. The catalyst concentration is the same as described previously. This reaction yields an organoalkoxysilane or siloxane compound containing at least one alkoxysilane moiety or functionality, such as those described herein.

In yet another embodiment, the new siloxane bond is produced from a two step reaction of the organohydrosilane or siloxane compounds bearing at least one hydrosilane moiety with less than molar equivalent (compared to Si—H functionality) of a source of oxygen. The source of oxygen may be any compound that reacts with the organohydrosilane or siloxane compounds bearing at least one hydrosilane moiety to produce an organoalkoxysilane or siloxane compound containing at least one alkoxysilane moiety or functionality. The produced organoalkoxysilane or siloxane compound is subsequently reacting with the residual organohydrosilane or siloxane compound to form a new siloxane bond. The final resultant product is the compound as described herein, namely a compound containing a new silicon-oxygen bond $(M_aD_b\ T_cQ_d)_e(R^2)_f(R^3)_g SiOSi(R^4)_h(R^5)_i\ (M_a\ D_bT_cQ_d)_j$ and hydrocarbon $(CH_3R^1)$ as the products. When less than molar equivalent of the compound comprising oxygen e.g in the case of diethylether 0.5 molar equivalent is preferable, a high molecular weight siloxane results. In order to obtain low molecular weight siloxane, the oxygen source is provided at an amount that is higher than the molar equivalentpreferable.

The above reaction is generally accomplished in the presence of an appropriate catalyst. The catalyst for this reaction is preferably the same type of catalyst as described previously, namely the Lewis acid catalysts described herein and more preferably, $B(C_6F_5)_3$. The above reaction can be accomplished in ambient conditions or at elevated temperature. The catalyst concentration is the same as described previously.

Further, as described for a previous embodiment, reaction of siloxane oligomers and polymers that bear more than two (H—Si$\equiv$) functionality with less than molar equivalent, preferentially with 0.5 molarequivalent (compared to Si—H functionality) of a source of oxygen is also possible and will lead to a formation of the cross-linked network.

The compositions produced according to the method or process of this invention are useful in the field of siloxane elastomers, siloxane coatings, insulating materials and cosmetic products. The condensation reaction of ($\equiv$Si—H) terminated dimethylsiloxane oligomers with alkoxy-terminated diphenylsiloxane oligomers leads to a formation of regular block siloxane copolymers with beneficial thermo-mechanical properties. The crosslinked material produced via condensation of siloxane oligomers and polymers that bear more than one ($\equiv$SiOCH$_2$R$^1$) moiety with the siloxane oligomers and polymers having more than one (H—Si$\equiv$) functional group will lead to a formation of novel siloxane coatings and siloxane foams. A low cross-link density network frequently has the ability to be swollen by lower molecular weight siloxanes or hydrocarbons thereby forming a gel. Such gels have found utility as silicone structurants for cosmetic compositions. Hyperbranched siloxane polymers may be prepared by reacting the self-condensation of molecule that bears more than one ($\equiv$SiOCH$_2$R$^1$) and one (H—Si$\equiv$) functionalities in the presence of Lewis acid.

It is to be noted that silicon is a tetravalent element and for purposes of descriptive convenience herein, not all four bonds of the silicon atom have been described in some of the abbreviated chemical reaction scenarios used to explain the reaction chemistry involved in the formation of non-hydrolytic silicon oxygen bonds. Where silicon is hypovalent or hypervalent in terms of its customary stereochemistry, the full structure has been indicated.

Experimental

1. Reaction of $MD^H{}_{25}D_{25}M$ with $Me_2Si(OEt)_2$.

A 50 ml flask was charged with 7.5 g of $MD^H{}_{25}D_{25}M$ (0.057mol of Si—H) and 3 g of $Me_2Si(OEt)_2$ (0.02 mol). The resulting low viscosity homogenous fluid was heated to 100 g for 1 hr. No reaction was observed. This example demonstrates that the reaction requires appropriate catalysis.

2. Reaction of $MD^H{}_{25}D_{25}M$ with $MeSi(OEt)_3$ in the Presence of $B(C_6F_5)_3$ A 50 ml flask was charged with 7.5 g of $MD^H{}_{25}M$ (0.057 mol of Si—H) and 3 g of MeSi(OEt)3 (0.02 mol). The reagents were mixed to form a low viscosity homogenous fluid. 1000 ppm of $B(C_6F_5)_3$ as a 1.0 wt % solution in methylene chloride, was added to the flask. The resulting mixture was stable at room temperature for several hours. After heating to 80° C. a very violent reaction occurred with rapid evolution of gas. The reaction mixture turned into foam in few seconds. This example shows that addition of a suitable borane catalyst, $B(C_6F_5)_3$, promotes an rapid reaction between Si—H and SiOR. Conceivably this system could be used to make a siloxane foam.

3. Self Condensation of $(CH_3)_2Si(H)(OC_2H_5)$

A 50 ml flask was charged with 10 g of dry toluene and $5.0\times10^{-6}$ moles of $B(C_6F_5)_3$. The resulting mixture was heated to 50° C. Next 5.2 g (0.05 moles) of $(CH_3)_2Si(H)(OEt)$ was added dropwise over a period of 30 minutes. The exothermic reaction with gas evolution stared after addition of first few drops of alkoxy silane. The rate of addition was adjusted to keep the reaction mixture temperature below 90° C. After addition was completed, the resulting mixture was heated at 50° C. for an additional 60 minutes. The proton NMR showed 100% conversion of Si—H and 90% conversion of Si—OEt. $Si^{29}$ NMR indicated the formation of linear alkoxy-stopped siloxane oligomers along with small amounts of $D_3$ (hexamethylcyclotrisiloxane) and $D_4$ (octamethyl cyclotetrasiloxane). This low temperature process may also be carried out a room temperature.

4. Self Condensation of $(CH_3)Si(H)(OCH_3)_2$

A 50 ml flask was charged with 10 g of dry toluene and $5.0\times10^{-6}$ moles of $B(C_6F_5)_3$. The resulting mixture was heated to 50° C. Next 5.3 g (0.05 moles) of $(CH_3)Si(H)(OCH_3)_2$ was added dropwise over a period of 30 minutes. The exothermic reaction with gas evolution started after the addition of the first few drops of alkoxy silane. The rate of addition was adjusted to keep a mixture temperature below 90° C. After addition was completed, the resulting mixture was heated at 50° C. for an additional 60 minutes. The proton NMR showed 100% conversion of Si—H and 50% conversion of Si—$OCH_3$. $Si_{29}$ NMR indicated formation of hyperbranched siloxane oligomers with Si—$OCH_3$ end groups.

5. Self Condensation of $HSi(OC_2H_5)_3$

A 50 ml flask was charged with 10 g of dry toluene and $5.0\times10^{-6}$ moles of $B(C_6F_5)_3$. The resulting mixture was heated to 50° C. Next 7.9 g (0.05 moles) of $HSi(OC_2H_5)_3$ was added drop wise over a period of 30 minutes. The reaction temperature did not change, any gas evolution was observed. After addition of alkoxysilane was completed the resulting mixture was heated at 50° C. for an additional 60 minutes. The proton NMR showed 0% conversion of Si—H.

6. Condensation of $(CH_3O)_2Si(C_6H_5)_2$ with H—$Si(CH_3)_2$—O—$Si(CH_3)_2$—H

A 50 ml flask was charge with 10 g of dry toluen and $5.0\times10^{-6}$ moles of $B(C_6F_5)_3$.

The resulting mixture was heated to 50° C. Next a mixture of 4.88 g (0.02 moles) of $(CH_3O)_2Si(C_6H_5)_2$ and 2.68 g (0.02 moles) of H—$Si(CH_3)_2$—O—$Si(CH_3)_2$—H was added drop wise over a period of 30 minutes. The exothermic reaction with gas evolution stared after addition of the first few drops. After addition was completed the resulting mixture was heated at 50° C. for an additional 60 minutes. The proton NMR showed 100% conversion of Si—H and 100% conversion of Si—$OCH_3$. $Si^{29}$ NMR indicated formation of cyclic compound $(Si(C_6H_5)_2$—O $Si(CH_3)_2$—O—$Si(CH_3)_2$—O)—and linear oligomers.

7. Condensation of $(CH_3O)_2Si(C_6H_5)_2$ with H—$Si(CH_3)_2$—Cl

A 50 ml flask was charged with 10 g of dry toluene, 2.93 g (0.03 moles) of $HSi(CH_3)_2$—Cl and $5.0\times10^{-6}$ moles of $B(C_6F_5)_3$ and cooled down to 20° C. Next a mixture of 3 g (0.012 moles) of $(CH_3O)_2Si(C_6H_5)_2$ and 3.0 g of toluene was added drop wise over a period of 30 minutes. The exothermic reaction with gas evolution stared after addition of the first drop. After addition was completed the resulting mixture was heated at 50° C. and low boiling components were stripped by application of a partial vacuum. The proton NMR showed 100% conversion of Si—H and formation of chloro-stopped siloxane (ClSi$(CH_3)_2$—O—$S(C_6H_5)_2$—O—$Si(CH_3)_2$Cl). $Si^{29}$ NMR confirmed formation of this compound.

8. Condensation of $((CH_3)_2CHO)_2SiC_2H_3$ with H—$Si(CH_3)_2$—O—$Si(CH_3)_2$—H A 50 ml flask was charged with 10 g of dry toluene and $5.0\times10^{-6}$ moles of $B(C_6F_5)_3$. The resulting mixture was heated to 50° C. Next a mixture of 4.64 g (0.02 moles) of $(iPrO)_3SiVi$ and 1.34 g (0.01 mol) of H—$Si(CH_3)_2$—O—$Si(CH_3)_2$—H was added drop wise over a period of 5 minutes. The reaction temperature did not change, and no gas evolution was observed. After addition of regents was completed the resulting mixture was heated at 50° C. for additional 60 min. The GC analysis did not show formation of siloxane oligomers. Example 8 shows that sterically hindered alkoxysilanes such as isopropoxysilane or t-butyloxysilane do not react with Si—H in the presence of $B(C6F_5)_3$ The condensation reaction requires the presence of —O—$CH_2$—$R^1$ alkoxide moiety attached to silicon atom.

9. Reaction of $MD^H{}_{25}D_{25}M$ with $MeSi(OMe)_3$ in the Presence of $B(C_6F_5)_3$ A 10 ml flask was charged with 1.25 g of $MD^H{}_{25}D_{25}M$ (0.01 moles of Si—H) and an appropriate amount of MeSi(OMe)3. The reagents were mixed to form a low viscosity homogenous fluid. Next 160 ppm of $B(C_6F_5)_3$ was added. The cure kinetics of the above mixture was evaluated by differential scanning calorimetry (DSC: Perkin Elmer). The observed pot life, peak temperature and Delta H are presented in the following table:

| Exp. # | Formula | SiH/SiOR | Peak temp | Delta H J/g | Pot life/min |
|---|---|---|---|---|---|
| 091-c | 884466-MeSi(OMe)3 | 0.63 | 53.4 | 561 | >360 |
| 091-d | 884466-MeSi(OMe)3 | 1.8 | 61.5 | 174 | 45 |
| 091-e | 884466-MeSi(OMe)3 | 1 | 57.4 | 310 | >360 |

10. Reaction of $MD^H{}_{25}D_{25}M$ with $OctylSi(OMe)_3$ in the Presence of $B(C_6F_5)_3$ A 10 ml flask was charged with 1.25 g of $MD^H{}_{25}D_{25}M$ (0.01 moles of Si—H) and appropriate amount of $(C_8H_{17})Si(OMe)_3$. The reagents were mixed to form a low viscosity homogenous fluid. Next 160 ppm of $B(C_6F_5)_3$ was added. The cure kinetics of the above mixture was evaluated by differential scanning calorimetry (DSC: Perkin Elmer). The observed pot life, peak temperature and Delta H are presented in the following table:

| Exp. # | Formula | SiH/SiOR | Peak temp | Delta H J/g | Pot life/min |
|---|---|---|---|---|---|
| O91-f | 884466-OctSi(OMe)3 | 1 | 47.5 | 745 | 20 |
| O91-g | 884466-OctSi(OMe)3 | 0.66 | 62 | 196 | 20 |
| O91-h | 884466-OctSi(OMe)3 | 1.25 | 36.7 | 490 | 10 |

Examples 9 and 10 show that a mixture of Si—H siloxane with alkoxysilane in the presence of a catalytic amount of $B(C_6F_5)_3$ is stable at room temperature for a period ranging from 10 min to more than 6 hours. The room temperature stable mixture can be quickly reacted at slightly elevated temperature. These experiments indicate that the mixtures from examples 9 and 10 could be used to produce thin siloxane coatings at a low temperature (below 80° C.). Such properties would be useful for low temperature paper release coatings and applications thereof.

11. Preparation of 1,4-bis(disilyl)benzene with Diethylether.

A 50 ml 3-neck flask equipped with a stir bar, condenser, thermometer and rubber septum seal was evacuated and then filled back with nitrogen. The flask was charged via glass syringe with 10 ml toluene, 9.88 g (0.0515 mols) of 1,4-bis (dimethylsilyl)benzene and 0.0015 g of B(C6F5)3. 3.7 g (0.05 mols) of diethylether were added dropwise via glass syringe over a period of three hours. The condensation reaction started after addition of a few drops of diethylether. The start reaction was indicated by an increase of the temperature of the reaction mixture from 25° C. to 32° C. and release of gaseous byproduct. At the end of the additional step, an additional 0.001 g of catalyst was added. After one hour of mixing at 25° C., the reaction mixture was poured to 100 ml of methanol. The precipitation of polymeric material was observed immediately. The polymeric fraction was subsequently dried on the vacuum line to yield 10 g (95%) of white crystalline solid. GPC analysis indicated a Mw of 26000 and Mw/Mn of 2.3.

12. Reaction of 1,1,3,3-tetramethyldisiloxane (TMDS) with ethyl acetate

A solution of TMDS, 2.00 g (14.9 mmol) in 10 ml of ethyl acetate was added slowly to a solution of $B(C_6F_5)_3$, 10.0 mg (0.0195 mmol) in 35 ml of ethyl acetate. Upon initial addition, no gas evolution was noted but when about 50% of the TMDS had been added, rapid gas evolution accompanied by a strong exothermic reaction occurred. When addition of the silane was complete and gas evolution had ceased volatiles were removed under vacuum affording 2.42 g of an oil. Analysis of this oil by $^1H$ and Si NMR and by GC-MS indicated it to be a mixture of cyclic siloxanes and ethoxy-capped linear siloxanes having an average composition of about 3 silicon atoms per ethoxy group.

13. Reaction of 1,1,3,3-tetramethyldisiloxane (TMDS) with Methyl Acetate

A solution of TMDS, 2.00 g (14.9 mmol) in 10 ml of methyl acetate was added slowly to a solution of $B(C_6F_5)_3$, 10.0 mg (0.0195 mmol) in 35 ml of methyl acetate. Upon initial addition, no gas evolution was noted but when about 50% of the TMDS had been added, rapid gas evolution accompanied by a strong exothermic reaction occurred. When addition of the silane was complete and gas evolution had ceased volatiles were removed under vacuum affording an oil. Analysis of this oil by H and Si NMR and by GC-MS indicated it to be a mixture of cyclic siloxanes and a mixture of methoxy and ethoxy-capped linear siloxanes (methoxy/ethoxy~1/1).

14. Reaction of 1,1,3,3-tetramethyldisiloxane (TMDS) with Dimethyl Carbonate

A solution of TMDS, 2.00 g (14.9 mmol) in 10 ml of dimethyl carbonate was added slowly to a solution of $B(C_6F_5)_3$, 10.0 mg (0.0195 mmol) in 35 ml of dimethylcarbonate. Upon initial addition, some gas evolution was noted accompanied by a strong exothermic reaction. When addition of the silane was complete and gas evolution had ceased volatiles were removed under vacuum affording 1.1 g of an oil. Analysis of this oil by H and Si NMR and by GC-MS indicated it to be a mixture of short linear methoxy stopped siloxanes the main component of which is 1,5-dimethoxy-1,1,3,3,5,5-hexamethyltrisiloxane.

15. Preparation of poly-2,6,2'6'-tetramethylbiphenoxy-1,1,3, 3, tetramethyldisiloxanyl Ether To a stirred mixture of 24.2 g (0.1 mol) of tetramethylbiphenol and 55 mg (0.0001 mol) of tris-pentafluorophenyl boron in 60 ml of $CH_2Cl_2$ was added over 50 minutes a solution of tetramethyldisiloxane in 40 ml of $CH_2Cl_2$. Gas evolved vigorously with each drop of silane added and the mixture became viscous near the end of the addition. The polymer was isolated as a gummy mass by precipitation into isopropyl alcohol. The molecular weight of the polymer was determined by gel permeation to be; Mw=108,000/Mn=51, 800. The Tg of the polymer is 54° C. by DSC. A thin film of the polymer, obtained by compression molding at 150° C. did not ignite when exposed to a burning match.

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents referenced herein are herewith and hereby specifically incorporated by reference.

Having described the invention, that which is claimed is:

1. A process for forming a silicon to oxygen bond comprising:
  a) reacting a first silicon containing compound said first silicon containing compound comprising a hydrogen atom directly bonded to a silicon atom with
    i) at least one compound comprising oxygen, said compound selected from the group consisting of alcohol, ester, aldehyde, ether, carbonate and combinations and mixtures thereof and
    ii) a Lewis acid catalyst,
  thereby forming a second silicon containing compound, said second silicon containing compound comprising an alkoxy group bonded to a silicon atom; and
  b) reacting the formed second silicon containing compound comprising an alkoxy group bonded to a silicon atom with the residual first silicon containing compound thereby forming a silicon to oxygen bond, and wherein said process is stabilized by the addition of a compound selected from the group consisting of ammonia, primary amines, secondary amines, tertiary amine and organophosphines.

2. The process of claim 1 wherein the Lewis acid catalyst comprises a compound of the formula:

$$MR^{12}_x X_y$$

wherein M is selected from the group consisting of B, Al, Ga, In and Tl; each $R^{12}$ is independently selected from the group of monovalent aromatic hydrocarbon radicals having from 6 to 14 carbon atoms; X is a halogen atom selected from the group consisting of F, Cl, Br, and I; x is 1, 2, or 3; and y is 0, 1 or 2; subject to the requirement that x+y=3.

3. The process of claim 2 where M is boron.

4. The process claim 2 wherein each $R^{12}$ is $C_6F_5$ and x=3.

5. The process of claim 1 wherein said process is activated by heat.

6. A process for forming a silicon to oxygen bond comprising:

a) reacting a first silicon containing compound said first silicon containing compound comprising a hydrogen atom directly bonded to a silicon atom with i) at least one compound comprising oxygen, said compound selected from the group consisting of alcohol, ester, aldehyde, ether, carbonate and combinations and mixtures thereof and ii) a Lewis acid catalyst, thereby forming a second silicon containing compound, said second silicon containing compound comprising an alkoxy group bonded to a silicon atom; and b) reacting the formed second silicon containing compound comprising an alkoxy group bonded to a silicon atom with the residual first silicon containing compound thereby forming a silicon to oxygen bond, and wherein the compound comprising oxygen is an ether.

7. The process of claim 6 wherein the ether is diethylether.

8. A process for forming a silicon to oxygen bond comprising:

a) reacting a first silicon containing compound said first silicon containing compound comprising a hydrogen atom directly bonded to a silicon atom with i) at least one compound comprising oxygen, said compound selected from the group consisting of alcohol, ester, aldehyde, ether, carbonate and combinations and mixtures thereof and ii) a Lewis acid catalyst having the formula $B(C_6F_5)_3$, thereby forming a second silicon containing compound, said second silicon containing compound comprising an alkoxy group bonded to a silicon atom; and b) reacting the formed second silicon containing compound comprising an alkoxy group bonded to a silicon atom with the residual first silicon containing compound thereby forming a silicon to oxygen bond, and wherein the compound comprising oxygen is an ether.

* * * * *